United States Patent
Umebayashi (10) Patent No.: US 9,073,230 B2
(45) Date of Patent: Jul. 7, 2015

(54) METHOD FOR CONTROLLING CONVEYANCE SPEED OF SHEET, METHOD FOR MANUFACTURING WEARING ARTICLE, APPARATUS FOR MANUFACTURING WEARING ARTICLE, AND WEARING ARTICLE

(75) Inventor: Toyoshi Umebayashi, Settsu (JP)

(73) Assignee: ZUIKO CORPORATION (JP)

( * ) Notice: Subject to any disclaimer, the term of this patent is extended or adjusted under 35 U.S.C. 154(b) by 832 days.

(21) Appl. No.: 13/378,468

(22) PCT Filed: Jun. 23, 2009

(86) PCT No.: PCT/JP2009/061414
§ 371 (c)(1),
(2), (4) Date: Dec. 15, 2011

(87) PCT Pub. No.: WO2010/150357
PCT Pub. Date: Dec. 29, 2010

(65) Prior Publication Data
US 2012/0090071 A1    Apr. 19, 2012

(51) Int. Cl.
*A61F 13/15*    (2006.01)
*B32B 41/02*    (2006.01)
*B65H 35/08*    (2006.01)
*B26D 5/32*    (2006.01)
(Continued)

(52) U.S. Cl.
CPC .............. *B26D 5/32* (2013.01); *Y10T 83/536* (2015.04); *Y10T 83/04* (2015.04); *Y10T 156/1097* (2015.01); *Y10T 156/12* (2015.01); *Y10T 156/1085* (2015.01); *Y10T 156/10* (2015.01); *Y10T 156/1077* (2015.01); *B29C 66/93451* (2013.01); *B29C 66/934* (2013.01); *A61F 13/15723* (2013.01); *A61F 13/15739* (2013.01); *A61F 13/15756* (2013.01); *A61F 13/15772* (2013.01); *B26D 1/626* (2013.01); *B26D 5/34* (2013.01); *B65H 35/08* (2013.01); *B65H 2513/102* (2013.01); *B65H 2513/11* (2013.01); *B65H 2513/50* (2013.01)

(58) Field of Classification Search
CPC ........................... B32B 41/00; B32B 2041/04
USPC ........... 156/64, 265, 270, 519, 522, 351, 353, 156/361; 83/367, 76
See application file for complete search history.

(56) References Cited

U.S. PATENT DOCUMENTS 5,045,135 A    9/1991    Meissner et al.
5,286,317 A *  2/1994    Treat et al. .............. 156/64
(Continued)

FOREIGN PATENT DOCUMENTS

JP    4-314443    11/1992
JP    11-502738    3/1999
(Continued)

*Primary Examiner* — Linda L Gray
(74) *Attorney, Agent, or Firm* — Gerald E. Hespos; Michael J. Porco; Matthew T. Hespos (57) ABSTRACT

A method for controlling a conveyance speed of a sheet comprises the steps of: setting a reference rotation angle; rotationally driving a drive motor (8) and a rotary cutter (15); detecting a marker (2a) of a backsheet (2); detecting a rotation angle of a rotary blade of a cutting member when the marker (2a) is detected; ascertaining an angular difference between the detected rotation angle and the reference rotation angle; and controlling rotational driving of the drive motor (8) to reduce the angular difference.

2 Claims, 6 Drawing Sheets

(51) Int. Cl.
　　　*B29C 65/00*　　　(2006.01)
　　　*B26D 1/62*　　　(2006.01)
　　　*B26D 5/34*　　　(2006.01)

(56) References Cited

U.S. PATENT DOCUMENTS

| | | |
|---|---|---|
| 5,659,538 A | 8/1997 | Stuebe et al. |
| 5,980,087 A | 11/1999 | Brandon et al. |
| 6,092,002 A | 7/2000 | Kastman et al. |
| 6,269,720 B1 | 8/2001 | Pelagatti |
| 6,732,778 B1 | 5/2004 | Machida et al. |
| 2003/0047273 A1 | 3/2003 | Kojo et al. |

FOREIGN PATENT DOCUMENTS

| | | |
|---|---|---|
| JP | 2000-502649 | 3/2000 |
| JP | 2001-29385 | 2/2001 |
| JP | 2001-517098 | 10/2001 |
| JP | 2002-512566 | 4/2002 |
| JP | 2005-80827 | 3/2005 |
| WO | 97/24094 | 7/1997 |

\* cited by examiner

METHOD FOR CONTROLLING CONVEYANCE SPEED OF SHEET, METHOD FOR MANUFACTURING WEARING ARTICLE, APPARATUS FOR MANUFACTURING WEARING ARTICLE, AND WEARING ARTICLE

BACKGROUND OF THE INVENTION

1. Field of the Invention

The present invention relates to a method for controlling conveyance speed of a sheet, a method for manufacturing a wearing article, an apparatus for manufacturing a wearing article, and a wearing article.

2. Description of the Related Art

A wearing article, such as a diaper or a sanitary napkin, is produced by laminating a plurality of continuous sheets formed of a nonwoven fabric, a film or the like, and subjecting the laminate to a given processing. For example, the processing includes placement of a member, such as an absorbent body or a tape onto a given area of a continuous sheet, and printing or ink application to form a graphic, pattern or the like for improving appearance, on a given area of a continuous sheet. In advance of laminating the continuous sheet subjected to such a processing to another continuous sheet, it is necessary that these continuous sheets are positionally adjusted, i.e., registered, with respect to each other.

JP 2001-517098, JP 2000-502649 and JP 2002-512566 disclose a control and a method for registering two continuous sheets. Specifically, JP 2001-517098, JP 2000-502649 and JP 2002-512566 disclose a technique for registering a first layer having a plurality of components, and a second layer having a plurality of reference marks, wherein, when one of the reference marks is out of position with respect to an associated one of the components, a speed of the first or second layer is adjusted.

However, the technique disclosed in JP 2001-517098, JP 2000-502649 and JP 2002-512566 is not premised on cutting the continuous sheets at a position adequate for the reference mark and the associated component. Specifically, JP 2001-517098, JP 2000-502649 and JP 2002-512566 do not disclose means for suppressing a misregistration between a target cutting position and an actual cutting position, which would otherwise occur in response to stretching and contraction of the continuous sheet. Therefore, in cases where an absorbent body, a tape or a pattern (hereinafter referred to as "processing component") is provided on a continuous sheet, a position of the processing component with respect to a cutting position (edge) of the continuous sheet will vary in each wearing article after the cutting, which makes it impossible to accurately produce wearing articles.

SUMMARY OF THE INVENTION

The present invention has been made to solve the above problem, and it is an object of the present invention to provide a method for controlling conveyance speed of a sheet, a method for manufacturing a wearing article and an apparatus for manufacturing a wearing article each making it possible to accurately manufacture wearing articles, and a wearing article.

According to one aspect of the present invention, there is provided a method for controlling a conveyance speed of a sheet, in a process of cutting the sheet being conveyed according to rotational driving of a driving roller at intervals of a given length by a cutting member having a rotary blade, in such a manner that each of a plurality of markers provided on the sheet correspondingly to respective ones of a plurality of cutting positions for the cutting by the cutting member and a corresponding one of the cutting positions have a given positional relationship. The method comprises: a setting step of setting a reference rotation angle as a rotation angle of the rotary blade for establishing the given positional relationship when each of the markers is detected at a detection position upstream of the cutting member in a conveyance direction of the sheet; a driving step of rotationally driving the driving roller and the cutting member; a first detection step of detecting each of the markers of the sheet at the detection position; a second detection step of detecting the rotation angle of the rotary blade of the cutting member when the marker is detected in the first detection step; an ascertaining step of ascertaining an angular difference between the reference rotation angle and the rotation angle detected in the second detection step; and a speed control step of controlling a rotation speed of the driving roller to reduce the angular difference ascertained in the ascertaining step.

According to another aspect of the present invention, there is provided a method for manufacturing a wearing article having a component mounted on a sheet by cutting the sheet being conveyed according to rotational driving of a driving roller, at intervals of a given length by a cutting member having a rotary blade. The method comprises: a setting step of setting a reference rotation angle which is a rotation angle of the rotary blade at a time when each of a plurality of markers provided on the sheet correspondingly to respective ones of a plurality of cutting positions for the cutting by the cutting member is detected at a detection position upstream of the cutting member in a conveyance direction of the sheet, and which is for allowing each of the markers and a corresponding one of the cutting positions to have a given positional relationship; a driving step of rotationally driving the driving roller and the cutting member; a mounting step of mounting the component onto the sheet at a position between the driving roller and the cutting member in the conveyance direction of the sheet; a first detection step of detecting each of the markers of the sheet at the detection position; a second detection step of detecting the rotation angle of the rotary blade of the cutting member when the marker is detected in the first detection step; an ascertaining step of ascertaining an angular difference between the reference rotation angle and the rotation angle detected in the second detection step; and a speed control step of controlling a rotation speed of the driving roller to reduce the angular difference ascertained in the ascertaining step.

According to yet another aspect of the present invention, there is provided an apparatus for manufacturing a wearing article having a sheet and a component mounted on the sheet. The apparatus comprises: a driving roller capable of conveying the sheet; a drive motor operable to rotationally drive the driving roller; a mounting unit capable of mounting the component onto the sheet; a cutting member having a rotary blade capable of cutting the sheet at given intervals according to the rotational driving; a first detection member provided between the driving roller and the cutting member and capable of detecting each of a plurality of markers provided on the sheet correspondingly to respective ones of a plurality of cutting positions for the cutting by the cutting member; a second detection member capable of detecting a rotation angle of the rotary blade of the cutting member; and a control device operable, based on respective detection results of the first detection member and the second detection member, to control a rotation speed of the drive motor in such a manner that each of the markers and a corresponding one of the cutting positions have a given positional relationship.

According to still another aspect of the present invention, there is provided a wearing article manufactured by the above apparatus.

The present invention makes it possible to accurately manufacture wearing articles.

DETAILED DESCRIPTION OF THE PREFERRED EMBODIMENTS

With reference to the accompanying drawings, the present invention will now be described based on an embodiment thereof. It should be understood that the following embodiment is a specific example of the present invention, but is not meant to limit the scope of the present invention.

Figure 1:
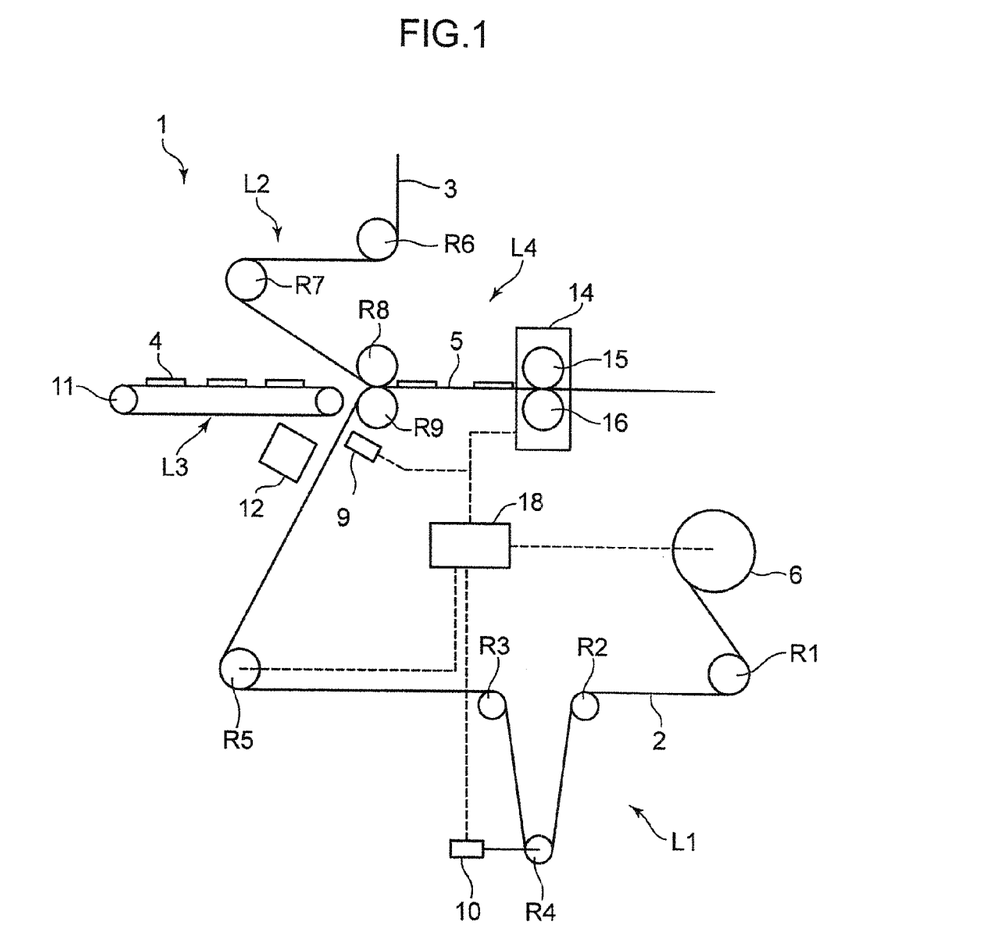
FIG. 1 is a schematic diagram illustrating a structure of a wearing article manufacturing apparatus according to one embodiment of the present invention.

FIG. 1 is a schematic diagram illustrating a structure of a wearing article manufacturing apparatus according to one embodiment of the present invention.

The manufacturing apparatus 1 is designed to manufacture a disposable diaper having an absorbent core 4. Specifically, the manufacturing apparatus 1 may be roughly divided into a line L1 for conveying a backsheet 2, a line L2 for conveying a topsheet 3, a line L3 for conveying the absorbent core 4, and a line L4 for conveying a joined assembly 5 of the backsheet 2 and the topsheet 3.

The line L1 is provided with: a roll 6 formed by winding the backsheet 2 therearound; three guide rollers R1 to R3 for conveying the backsheet 2 unrolled from the roll 6 along a given path; a dancer roller R4 for adding tension to the backsheet 2; a driving roller R5 for giving a driving force to the backsheet 2 so as to pull it from the roll 6; a roll motor 7 (see FIG. 7) for rotationally driving the roll 6; a drive motor 8 (see FIG. 3) for rotationally driving the driving roller R5; a marker detection sensor 9 capable of detecting markers provided on the backsheet 2; and a tension motor 10 for adjusting the tension to be added by the dancer roller R4. In the line L1, an operation of mounting an elastic member on the backsheet 2 in a stretched manner, and/or mounting a fixing tape or the like to the backsheet 2, is also performed, according to need.

Figure 2:
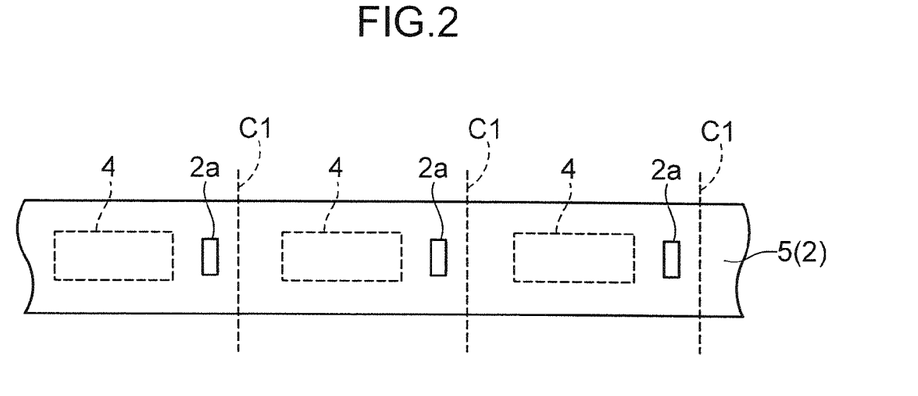
FIG. 2 is a top plan view schematically illustrating a state of a line L4 in FIG. 1.

The backsheet 2 to be conveyed in the line L1 is a sheet having liquid-impermeable properties (e.g., a sheet formed of a water-repellent nonwoven fabric, a plastic film or the like). As illustrated in FIG. 2, the backsheet 2 has a plurality of markers 2a provided thereon at the same intervals as those for a plurality of cutting positions C1 at which the backsheet 2 is to be cut by an aftermentioned cutting device 14. In this embodiment, each of the markers 2a includes a character, a graphic or figure, a symbol or a pattern printed on the backsheet 2. Alternatively, the marker 2a may be substituted by a component (e.g., a fixing tape) mounted on the backsheet 2 in the line L1.

The line L2 is provided with two guide rollers R6, R7 for conveying the topsheet 3 along a given path.

The topsheet 3 to be conveyed in the line L2 is a sheet having liquid-permeable properties (e.g., a sheet formed of a liquid-permeable nonwoven fabric, a perforated plastic film or the like). The topsheet 3 will be joined onto the backsheet 2 in the line L4 as described later.

The line L3 is provided with a conveyer 11 for conveying the absorbent core 4, and a mounting device (mounting unit) 12 for mounting the absorbent core 4 on the conveyer 11 onto the backsheet 2 being conveyed in the line L1. The mounting device 12 is adapted to join a plurality of generally rectangular-shaped absorbent cores 4 onto the backsheet 2 at the same intervals as those for the cutting positions C1, while allowing a longitudinal direction of each of the absorbent cores 4 to extend along a longitudinal direction of the backsheet 2, as illustrated in FIG. 2. More specifically, as illustrated in FIG. 2, the markers 2a will be provided on an outer surface (in FIG. 1, a lower surface) of the backsheet 2, and the absorbent cores 4 will be provided on an inner surface (in FIG. 1, an upper surface) of the backsheet 2.

For example, the absorbent cores 4 may be arranged at intervals in the following way. In a method employing a step of, on the conveyer 11, making cuts in a continuous body for configuring a plurality of absorbent cores 4 to form individual disconnected absorbent cores 4, the absorbent cores 4 can be arranged on the backsheet 2 at intervals by transferring each of the absorbent cores 4 from the conveyer 11 to the line L1 at a constant cycle using the mounting device 12, under a condition that a conveyance speed of the absorbent cores 4 by the conveyer 11 is set to become less than a conveyance speed of the backsheet 2 by the line L1. Alternatively, the mounting device 12 itself may be configured to have a function of arranging the absorbent cores 4 on the backsheet 2 at intervals (for example, the transportation apparatus described in WO 01/044086A may be employed).

Alternatively, each of the absorbent cores 4 may be directly transferred from the conveyer 11 to the line L4, while omitting the mounting device 12. Specifically, aftermentioned nip rollers R8, R9 provided in the line L4 are configured to have a function of suckingly holding each of the absorbent cores 4, so that it becomes possible to take each of the absorbent cores 4 from the conveyer 11 onto the backsheet 2 by the nip rollers R8, R9. In this case, the nip rollers R8, R9 configure the mounting unit.

The absorbent core 4 to be conveyed in the line L3 comprises a fluff pulp formed by crushing pulps, and may contain a superabsorbent polymer or the like.

The line L4 is provided with a pair of nip rollers R8, R9 for nipping the backsheet 2 and the topsheet 3 therebetween, and a cutting device 14 for cutting the backsheet 2 and the topsheet 3 at each of the cutting positions C1 (see FIG. 2). The nip rollers R8, R9 are disposed opposed to each other while interposing the joined assembly 5 of the backsheet 2 and the topsheet 3 therebetween, and adapted to be rotated individually so as to lead the joined assembly 5 toward a downstream side.

Figure 5:
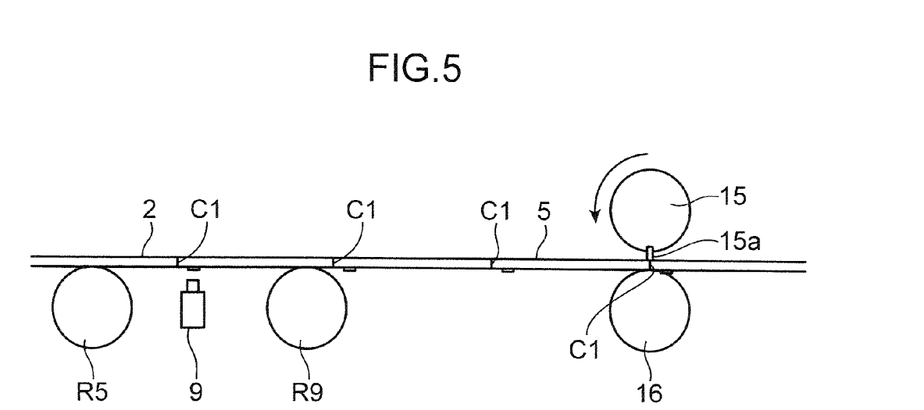
FIG. 5 is a side view schematically illustrating an operation of the control device, wherein a rotary blade is at a reference rotation angle.

As illustrated in FIG. 5, the cutting device 14 comprises a rotary cutter 15 having a rotary blade 15a, a counter roller 16 disposed opposed to the rotary cutter 15, a motor (not illustrated) for rotationally driving the rotary cutter 15, and an angle detection sensor 17 (see FIG. 3) including a rotary encoder for detecting a rotational position of the motor (i.e., a rotational position of the rotary blade 15*a*). The rotary cutter 15 and the counter roller 16 are disposed while interposing the joined assembly 5 of the backsheet 2 and the topsheet 3 therebetween, and adapted to be rotated in sync with each other so as to cut the joined assembly 5 by the rotary blade 15*a* every 360-degree rotation of the rotary blade 15*a*, while conveying the joined assembly 5.

Figure 3:
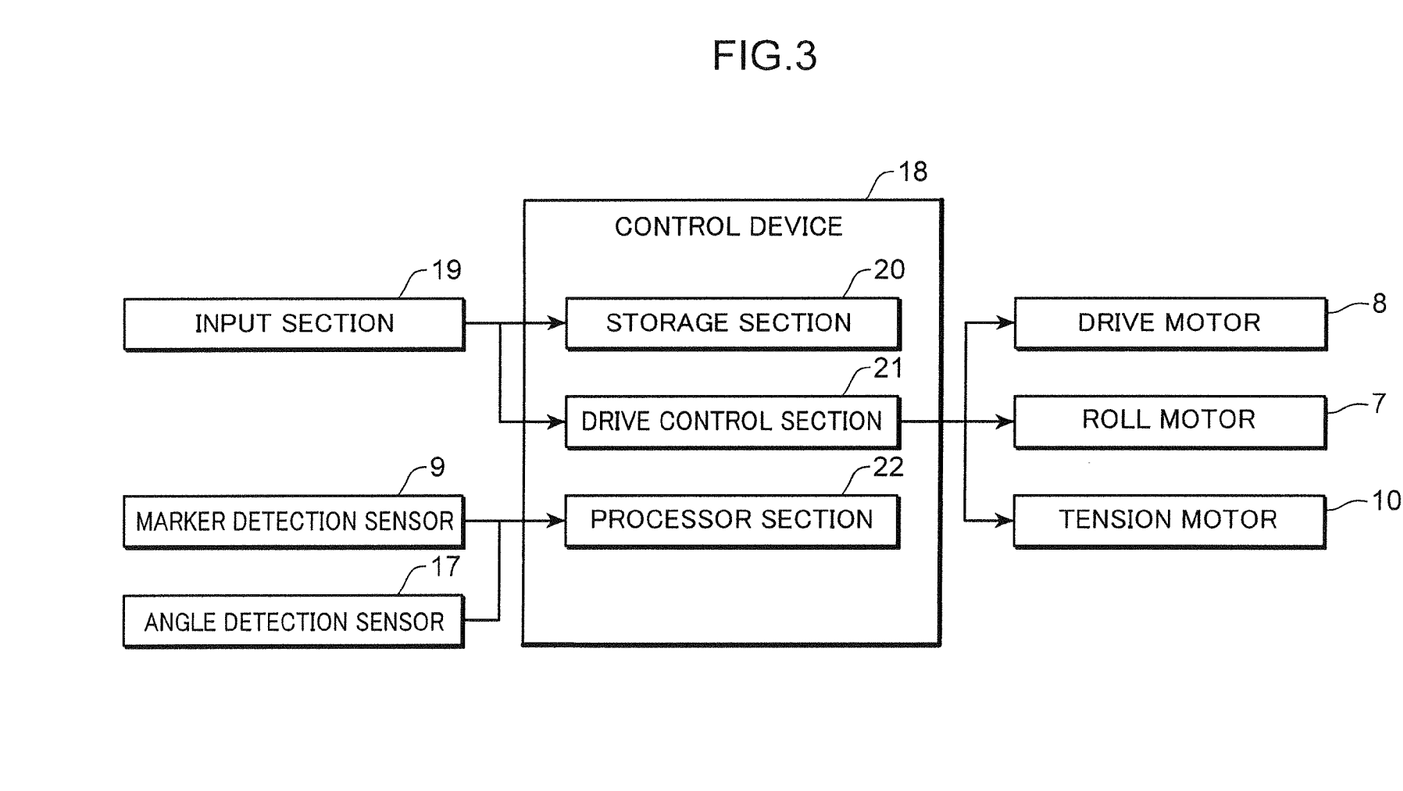
FIG. 3 is a block diagram illustrating an electrical configuration of a control device in FIG. 1.

The manufacturing apparatus 1 further comprises a control device 18 for controlling each of the above elements. FIG. 3 is a block diagram illustrating an electrical configuration of the control device 18 in FIG. 1.

Referring to FIGS. 1 and 3, the control device 18 is electrically connected to the drive motor 8, the roll motor 7, the tension motor 10, the marker detection sensor 9, and the angle detection sensor 17. The control device 18 is provided with an input section 19 for allowing an operator to input various settings therethrough.

Specifically, the control device 18 comprises a storage section 20, a drive control section 21, and a processor section 22.

The storage section 20 is used as a region for storing therein an initial setting, etc., and adapted to be capable of storing therein information output from the input section 19. Specifically, the storage section 20 stores therein a reference rotation angle which is a rotation angle of the rotary blade 15*a* for cutting the joined assembly 5 of the backsheet 2 and the topsheet 3 at each of the predetermined cutting positions C1. The reference rotation angle is a rotation angle of the rotary blade 15*a* of the rotary cutter 15 at a time when each of the markers 2*a* of the backsheet 2*a* is detected by the marker detection sensor 9. In other words, the reference rotation angle is preliminarily set on an assumption that, if a rotation angle of the rotary blade 15*a* at the time coincides with the reference rotation angle, the rotary blade 15*a* will reach each of the cutting positions C1 of the joined assembly 5. The storage section 20 further stores therein an estimated time period after one of the markers 2*a* (see FIG. 2) is detected by the marker detection sensor 9 through until a subsequent one of the remaining markers 2*a* is detected by the marker detection sensor 9. The estimated time period is determined by the conveyance speed of the backsheet 2, and the interval between the markers 2*a* provided on the backsheet 2.

The drive control section 21 is operable, based on the settings stored in the storage section 20 or an aftermentioned setting determined by the processor section 22, to drive the drive motor 8, the roll motor 7 and the tension motor 10. The drive control section 21 is also operable, in response to receiving a signal from the input section 19, to drive the drive motor 8, the roll motor 7 and the tension motor 10.

Figure 6:
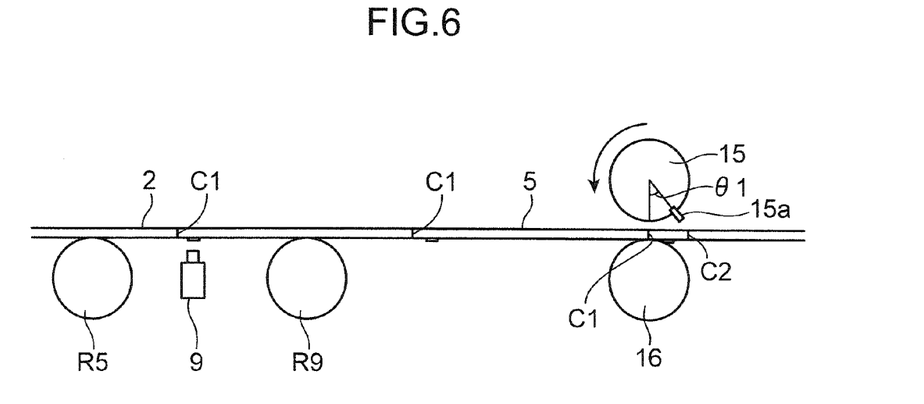
FIG. 6 is a side view schematically illustrating an operation of the control device, wherein an actual rotation angle of the rotary blade is advanced with respect to the reference rotation angle.
Figure 7:
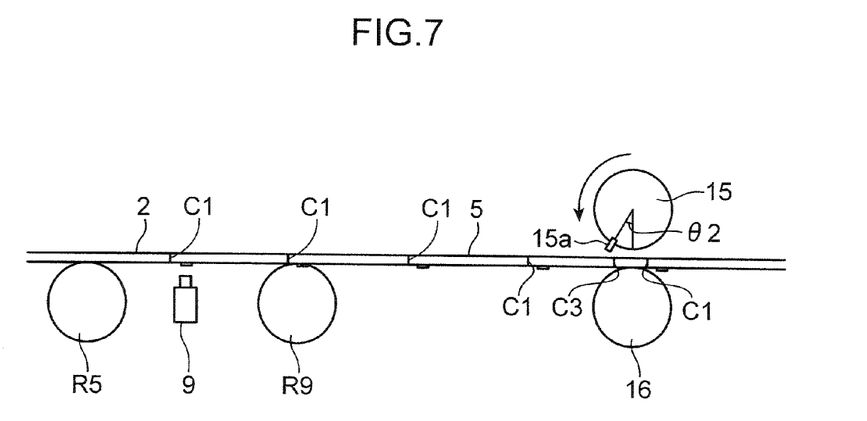
FIG. 7 is a side view schematically illustrating an operation of the control device, wherein the actual rotation angle of the rotary blade is retarded with respect to the reference rotation angle.

The processor section 22 is operable, based on respective detection results of the marker detection sensor 9 and the angle detection sensor 17, and the reference rotation angle stored in the storage section 20, to detect a difference between the reference rotation angle and an actual rotation angle of the rotary blade 15*a*. The processor section 22 is further operable to calculate a speed of the drive motor 8 for compensating for the difference in rotation angle during the estimated time period. With reference to FIGS. 5 to 7, details of processing to be performed by the processor section 22 will be described.

FIG. 5 illustrates a state in which the rotation angle of the rotary blade 15*a* at a time when one of the markers 2*a* is detected by the marker detection sensor 9 coincides with the reference rotation angle (rotation angle corresponding to one of the cutting positions C1 of the joined assembly 5).

FIG. 6 illustrates a state in which the rotation angle of the rotary blade 15*a* at a time when one of the markers 2*a* is detected by the marker detection sensor 9 is advanced with respect to the reference rotation angle by an angle θ1 (the joined assembly 5 is cut at a cutting position C2 downstream of the cutting position C1). Specifically, in the state illustrated in FIG. 6, due to fluctuation in tension to be applied to the joined assembly 5, the joined assembly 5 is stretched by an amount greater than expected, so that a conveyance position of the joined assembly 5 is relatively shifted backwardly with respect to the rotational position of the rotary blade 15*a*. In this case, the processor section 22 is operable to ascertain the angular difference θ1 based on the reference rotation angle, and output, to the drive control section 21, a command for relatively advancing a rotation angle of the drive motor 8 with respect to the rotation angle of the rotary blade 15*a* by the angle θ1 (a command for increasing the rotation speed of the drive motor 8) during the estimated time period from the present time (during a time period from the present time through until the subsequent marker 2*a* is detected). Specifically, in order to allow the state in FIG. 6 to be shifted to the state in FIG. 5 after an elapse of the estimated time period, it is necessary to satisfy a relationship represented by the following formula (1):

$$(w1 \times t \times 2\pi r1) - (w2 \times t \times 2\pi r2) = \theta1 \times t \times 2\pi r2 \quad (1)$$

In this formula, w1 is an angular speed (rad/s) of the drive motor 8, t is the estimated time period (s), and r1 is a radius of the driving roller R5, respectively. Further, w2 is an angular speed of the rotary cutter 15, and r2 is a radius of the rotary cutter 15. Based on the formula (1), the angular speed of the drive motor 8 is expressed as the following formula (2):

$$w1 = \{(\theta1 \times t \times 2\pi r2) + (w2 \times t \times 2\pi r2)\} \div (t \times 2\pi r1) \quad (2)$$

FIG. 7 illustrates a state in which the rotation angle of the rotary blade 15*a* at a time when one of the markers 2*a* is detected by the marker detection sensor 9 is retarded with respect to the reference rotation angle by an angle θ2 (the joined assembly 5 is cut at a cutting position C3 upstream of the cutting position C1). Specifically, in the state illustrated in FIG. 7, due to fluctuation in tension to be applied to the joined assembly 5, the joined assembly 5 is stretched by an amount less than expected, so that the conveyance position of the joined assembly 5 is relatively shifted forwardly with respect to the rotational position of the rotary blade 15*a*. In this case, the processor section 22 is operable to ascertain the angular difference θ2 based on the reference rotation angle, and output, to the drive control section 21, a command for relatively retarding the rotation angle of the drive motor 8 with respect to the rotation angle of the rotary blade 15*a* by the angle θ2 (a command for reducing the rotation speed of the drive motor 8) during the estimated time period from the present time. Specifically, in order to allow the state in FIG. 7 to be shifted to the state in FIG. 5 after the elapse of the estimated time period, it is necessary to satisfy a relationship represented by the following formula (3):

$$(w2 \times t \times 2\pi r2) - (w1 \times t \times 2\pi r1) = \theta2 \times t \times 2\pi r2 \quad (3)$$

Based on the formula (3), the angular speed of the drive motor 8 is expressed as the following formula (4):

$$w1 = \{(w2 \times t \times 2\pi r2) - (\theta2 \times t \times 2\pi r2)\} \div (t \times 2\pi r1) \quad (4)$$

In this embodiment, the reference rotation angle may be set as a given range. Specifically, the processor section 22 is operable, when an actual rotation angle falls within the given range, to output, to the drive control section 21, a command for keeping the speed of the drive motor 8 constant, even if the reference rotation angle and the actual rotation angle do not coincide with each other.

Figure 4:
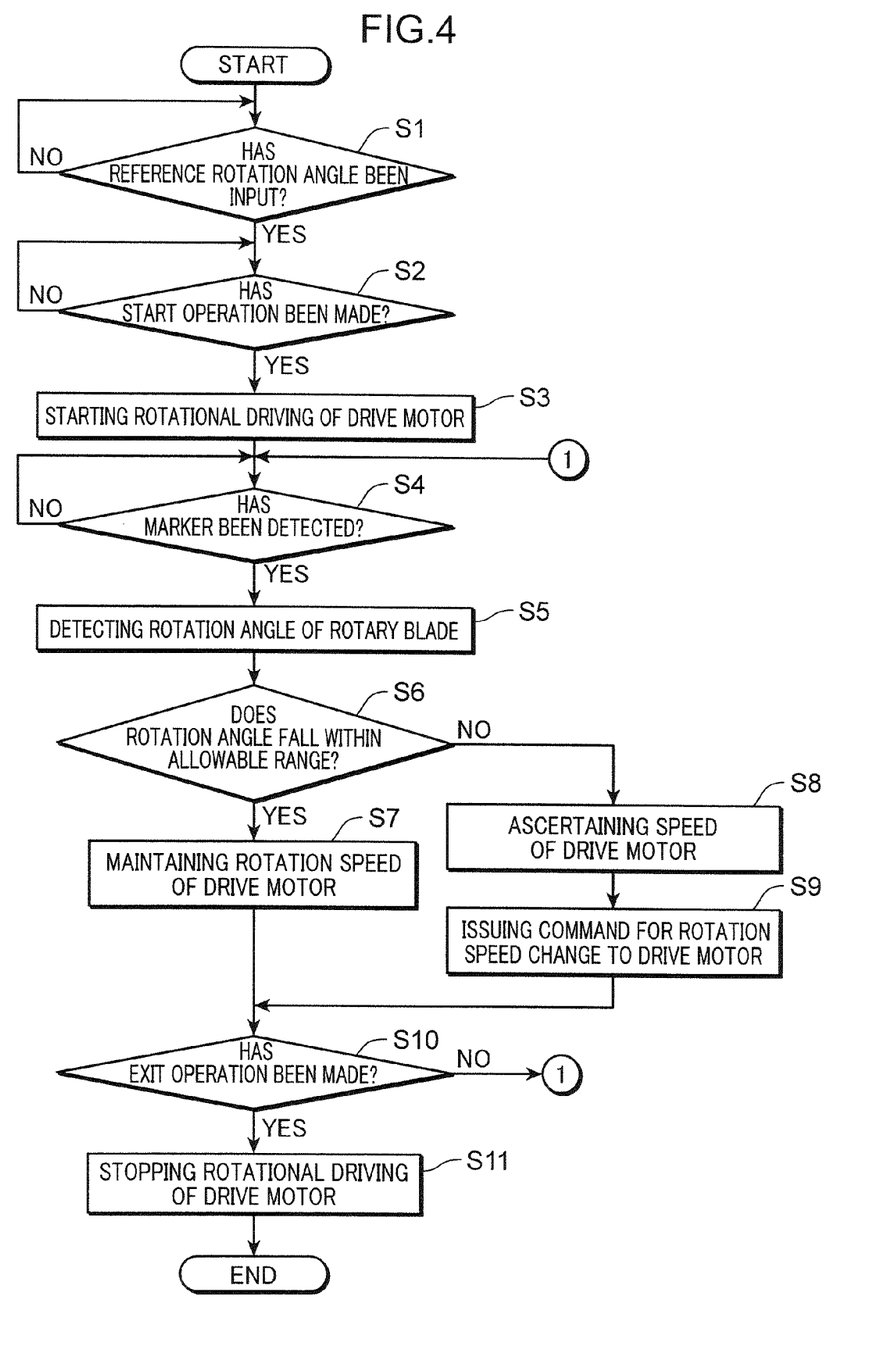
FIG. 4 is a flowchart illustrating a process to be executed by the control device in FIG. 1.

With reference to FIG. 4, a process to be executed by the control device 18 will be described below.

Upon start of the process by the control device 18, a standby state is continued while checking whether the reference rotation angle has been input (Step S1). Specifically, it is determined whether the reference rotation angle (a rotation angle and an allowable range thereof) has been input through the input section 19.

When it is determined that the reference rotation angle has been input (YES in the Step S1), it is determined whether a start operation has been made using the input section 19 (Step S2). When it is determined that the start operation has not been made (NO in the Step S2), the processing in the Step S2 will be repeatedly performed.

On the other hand, when it is determined that the start operation has been made (YES in the Step S2), the rotational driving of the drive motor 8 and the rotary cutter 15 is started (Step S3), and then it is determined whether one of the markers 2a has been detected (Step S4).

When it is determined that any one of the markers 2a has not been detected (NO in the Step S4), the processing in the Step S4 will be repeatedly performed. On the other hand, when it is determined that one of the markers 2a has been detected (YES in the Step S4), the rotation angle of the rotary blade 15a is detected (Step S5).

Then, it is determined whether the rotation angle of the rotary blade 15a falls within the allowable range of the reference rotation angle (Step S6). When it is determined that the rotation angle falls within the allowable range (YES in Step the S6), the rotation speed of the drive motor 8 is maintained (Step S7).

On the other hand, when it is determined that the rotation angle of the rotary blade 15a deviates beyond the allowable range (NO in Step the S6), a direction of deviation in rotation angle (FIG. 6: advance side, FIG. 7: retard side) and a difference in rotation angle (FIG. 6: θ1, FIG. 7: θ2) as illustrated in FIGS. 6 and 7 are ascertained, and then the speed of the drive motor 8 is ascertained based on the formulas (2) and (4) (Step S8). After the Step S8, a command for speed change is output to the drive motor 8 (Step S9).

After the Steps S7 and S9, it is determined whether an exit operation has been made using the input section 19 (Step S10). When it is determined that the exit operation has not been made (NO in the Step S10), the processing in the Step S4 will be repeatedly performed.

On the other hand, when it is determined that the exit operation has been made (YES in the Step S10), the driving of the drive motor 8 is stopped (Step S11), and the process is terminated.

As described above, the manufacturing apparatus 1 is designed such that the rotation speed of the drive motor 8 is controlled by the control device 18 to reduce a difference between the reference rotation angle and a rotation angle detected by the angle detection sensor 17. Thus, a conveyance speed of the backsheet 2 with respect to the rotary blade 15a can be adjusted in an adequate direction every time each of the markers 2a is detected, and thereby the cutting position with respect to the marker can be adequately set.

Therefore, the manufacturing apparatus 1 makes it possible to accurately manufacture an absorbent body.

Specifically, in disposable diapers manufactured by the manufacturing apparatus 1, a position of each of the absorbent body 4 and the tape or print provided on the backsheet 2 becomes generally uniform among the disposable diapers. Thus, it becomes possible to suppress individual variations in appearance and usability of the disposable diapers.

The above manufacturing apparatus 1 is designed such that an angular range is set as the reference rotation angle (the Step S1), and, when a rotation angle detected by the angle detection sensor 17 falls within the angular range (when YES in the Step S6), the rotation speed of the drive motor 8 is kept constant (the Step S7), which means that it is possible to set a range where the speed control for the drive motor 8 can be omitted. This makes it possible to facilitate simplification in control.

The above manufacturing apparatus 1 is designed to ascertain a rotation speed of the drive motor 8 for compensating for a difference between the reference rotation angle and the actual rotation angle, during the estimated time period, so that it becomes possible to compensate for the difference in rotation angle, after an elapse of the estimated time period.

The above manufacturing apparatus 1 comprises the input section 19, so that a value of the reference rotation angle to be stored in the storage section 20 can be input depending on types of disposable diapers and characteristics of the sheet.

The above specific embodiment primarily includes inventions having the following features.

According to one aspect of the present invention, there is provided a method for controlling a conveyance speed of a sheet, in a process of cutting the sheet being conveyed according to rotational driving of a driving roller at intervals of a given length by a cutting member having a rotary blade, in such a manner that each of a plurality of markers provided on the sheet correspondingly to respective ones of a plurality of cutting positions for the cutting by the cutting member and a corresponding one of the cutting positions have a given positional relationship. The method comprises: a setting step of setting a reference rotation angle as a rotation angle of the rotary blade for establishing the given positional relationship when each of the markers is detected at a detection position upstream of the cutting member in a conveyance direction of the sheet; a driving step of rotationally driving the driving roller and the cutting member; a first detection step of detecting each of the markers of the sheet at the detection position; a second detection step of detecting the rotation angle of the rotary blade of the cutting member when the marker is detected in the first detection step; an ascertaining step of ascertaining an angular difference between the reference rotation angle and the rotation angle detected in the second detection step; and a speed control step of controlling a rotation speed of the driving roller to reduce the angular difference ascertained in the ascertaining step.

In the control method, the rotation speed of the driving roller can be controlled to come close to the reference rotation angle set in such a manner each of the markers and a corresponding one of the cutting positions have a given positional relationship, so that a conveyance speed of the sheet with respect to the rotary blade can be adjusted in an adequate direction every time each of the markers is detected, and thereby the cutting position with respect to the marker can be adequately set.

Thus, the use of the control method makes it possible to accurately manufacture a wearing article.

Preferably, in the control method, the setting step includes setting an angular range as the reference rotation angle, wherein the speed control step includes, when the rotation angle detected in the second detection step falls within the angular range, keeping the rotation speed of the driving roller constant, irrespective of the angular difference ascertained in the ascertaining step.

This control method makes it possible to facilitate simplification of the method by setting a range where the speed control for the drive roller can be omitted. Specifically, in the above control method, as long as an actual positional relationship between each of the markers and a corresponding one of the cutting positions falls within a given range, the rotation speed control for the driving roller can be omitted even if the actual positional relationship is out of a target positional relationship.

According to another aspect of the present invention, there is provided a method for manufacturing a wearing article having a component mounted on a sheet by cutting the sheet being conveyed according to rotational driving of a driving roller, at intervals of a given length by a cutting member having a rotary blade. The method comprises: a setting step of setting a reference rotation angle which is a rotation angle of the rotary blade at a time when each of a plurality of markers provided on the sheet correspondingly to respective ones of a plurality of cutting positions for the cutting by the cutting member is detected at a detection position upstream of the cutting member in a conveyance direction of the sheet, and which is for allowing each of the markers and a corresponding one of the cutting positions to have a given positional relationship; a driving step of rotationally driving the driving roller and the cutting member; a mounting step of mounting the component onto the sheet at a position between the driving roller and the cutting member in the conveyance direction of the sheet; a first detection step of detecting each of the markers of the sheet at the detection position; a second detection step of detecting the rotation angle of the rotary blade of the cutting member when the marker is detected in the first detection step; an ascertaining step of ascertaining an angular difference between the reference rotation angle and the rotation angle detected in the second detection step; and a speed control step of controlling a rotation speed of the driving roller to reduce the angular difference ascertained in the ascertaining step.

In the manufacturing method, the rotation speed of the driving roller can be controlled to come close to the reference rotation angle set in such a manner that each of the markers and a corresponding one of the cutting positions have a given positional relationship, so that a conveyance speed of the sheet with respect to the rotary blade can be adjusted in an adequate direction every time each of the markers is detected, and thereby the cutting position with respect to the marker can be adequately set.

Thus, the manufacturing method makes it possible to accurately cut the sheet on which a component is mounted through the mounting step, and therefore accurately manufacture a wearing article.

Preferably, in the manufacturing method, the setting step includes setting an angular range as the reference rotation angle, and wherein the speed control step includes, when the rotation angle detected in the second detection step falls within the angular range, keeping the rotation speed of the driving roller constant, irrespective of the angular difference ascertained in the ascertaining step.

This manufacturing method makes it possible to facilitate simplification of the method by setting a range where the speed control for the drive motor can be omitted. Specifically, in the above manufacturing method, as long as an actual positional relationship between each of the markers and a corresponding one of the cutting positions falls within a given range, the rotation speed control for the driving roller can be omitted even if the actual positional relationship is out of a target positional relationship.

Preferably, in the manufacturing method, the mounting step includes mounting an absorbent core as the component onto the sheet, and wherein the manufacturing method further comprises a joining step of, after the mounting step, joining a second sheet onto the sheet to sandwich the absorbent core between the sheet and the second sheet.

This manufacturing method makes it possible to manufacture a wearing article having the absorbent core sandwiched between the pair of sheets.

According to yet another aspect of the present invention, there is provided an apparatus for manufacturing a wearing article having a sheet and a component mounted on the sheet. The apparatus comprises: a driving roller capable of conveying the sheet; a drive motor operable to rotationally drive the driving roller; a mounting unit capable of mounting the component onto the sheet; a cutting member having a rotary blade capable of cutting the sheet at given intervals according to the rotational driving; a first detection member provided between the driving roller and the cutting member and capable of detecting each of a plurality of markers provided on the sheet correspondingly to respective ones of a plurality of cutting positions for the cutting by the cutting member; a second detection member capable of detecting a rotation angle of the rotary blade of the cutting member; and a control device operable, based on respective detection results of the first detection member and the second detection member, to control a rotation speed of the drive motor in such a manner that each of the markers and a corresponding one of the cutting positions have a given positional relationship.

In the manufacturing apparatus, the rotation speed of the driving roller is controlled in such a manner that each of the markers and a corresponding one of the cutting positions have a given positional relationship, so that a conveyance speed of the sheet with respect to the rotary blade can be adjusted in an adequate direction every time each of the markers is detected, and thereby the cutting position with respect to the marker can be adequately set.

Thus, the manufacturing apparatus makes it possible to accurately cut the sheet on which a component is mounted, and therefore accurately manufacture a wearing article.

Preferably, in the manufacturing apparatus, the control device includes: a storage section storing therein a reference rotation angle which is a rotation angle of the rotary blade of the cutting member detected by the second detection member when the marker is detected by the first detection member, and which is preliminarily set in such a manner that each of the markers and a corresponding one of the cutting positions have the given positional relationship; a processor section operable to ascertain a difference between the reference rotation angle and the rotation angle of the rotary blade of the cutting member detected by the second detection member; and a drive control section operable to output a signal for changing the speed of the drive motor to reduce the difference in rotation angle, to the drive motor.

In this manufacturing apparatus, the speed of the driving roller is controlled to allow a rotation angle of the cutting member at a time when each of the markers is detected, to come close to the reference rotation angle, so that each of the markers and a corresponding one of the cutting positions can be set to an adequate positional relationship.

Preferably, in the above manufacturing apparatus, the storage section stores therein an angular range as the reference rotation angle, wherein the drive control section is operable, when the rotation angle detected by the second detection section falls within the angular range, to keep a driving speed of the drive motor constant, irrespective of the angular difference ascertained by the processor section.

This manufacturing apparatus makes it possible to facilitate simplification of the processing by the drive control section by setting a range where the speed control for the drive motor can be omitted. Specifically, in the above manufacturing apparatus, as long as an actual positional relationship between each of the markers and a corresponding one of the cutting positions falls within a given range, the rotation speed control for the driving roller can be omitted even if the actual positional relationship is out of a target positional relationship.

Preferably, in the above manufacturing apparatus, the storage section stores therein an estimated time period preliminarily set as a time period from a detection of one of the markers through until a detection of a subsequent one of the remaining markers, wherein the processor section is operable to ascertain a rotation speed of the drive motor for compensating for the difference in rotation angle during the estimated time period.

In this manufacturing apparatus, the rotation speed of the drive motor is set to a value ascertained by the processor section, so that a difference between the reference rotation angle and an actual rotation angle can compensate before the subsequent marker is detected.

Preferably, the above manufacturing apparatus further comprises an input section adapted to accept an operation by a user so as to allow the reference rotation angle to be input into the storage section therethrough.

This manufacturing apparatus makes it possible to input a value of the reference rotation angle to be stored in the storage section, depending on types of disposable diapers and characteristics of the sheet.

According to still another aspect of the present invention, there is provided a wearing article manufactured by the above apparatus.

The wearing article can be provided as a wearing article in which a positional relationship between the marker (component) and the cutting position is adequately set.

The present invention is suitably usable in manufacturing a wearing article, such as a disposable diaper or an absorbent body.

What is claimed is:

1. A method for manufacturing a wearing article having a component mounted on a sheet by cutting the sheet being conveyed according to rotational driving of a driving roller, at intervals of a given length by a cutting member having a rotary blade, the method comprising:
    a setting step of setting a reference rotation angle of the rotary blade at a time when each of a plurality of markers provided on the sheet correspondingly to respective ones of a plurality of cutting positions for the cutting by the cutting member is at a detection position upstream of the cutting member in a conveyance direction of the sheet, so that each of the markers and a corresponding one of the cutting positions have a given positional relationship;
    a driving step of rotationally driving the driving roller and the cutting member;
    a mounting step of mounting an absorbent core as the component onto the sheet at a position between the driving roller and the cutting member in the conveyance direction of the sheet;
    a joining step of joining a second sheet onto the sheet to sandwich the absorbent core between the sheet and the second sheet;
    a first detection step of detecting each of the markers of the sheet at the detection position;
    a second detection step of detecting the rotation angle of the rotary blade of the cutting member when the marker is detected in the first detection step;
    an ascertaining step of ascertaining an angular difference between the reference rotation angle and the rotation angle detected in the second detection step; and
    a speed control step of controlling a rotation speed of the driving roller to reduce the angular difference ascertained in the ascertaining step.

2. The method for manufacturing a wearing article according to claim 1, wherein the setting step includes setting an angular range as the reference rotation angle, and wherein the speed control step includes, when the rotation angle detected in the second detection step falls within the angular range, keeping the rotation speed of the driving roller constant, irrespective of the angular difference ascertained in the ascertaining step.

* * * * *